(12) United States Patent
Cole

(10) Patent No.: US 11,712,374 B2
(45) Date of Patent: Aug. 1, 2023

(54) BREATHABLE MEDICAL GAUZE PATCH

(71) Applicant: Sharon Ylonde Cole, Brooklyn, NY (US)

(72) Inventor: Sharon Ylonde Cole, Brooklyn, NY (US)

( * ) Notice: Subject to any disclaimer, the term of this patent is extended or adjusted under 35 U.S.C. 154(b) by 577 days.

(21) Appl. No.: 16/880,863

(22) Filed: May 21, 2020

(65) Prior Publication Data

US 2020/0368074 A1 Nov. 26, 2020

Related U.S. Application Data

(60) Provisional application No. 62/850,857, filed on May 21, 2019.

(51) Int. Cl.
*A61F 13/02* (2006.01)
*A61F 13/00* (2006.01)

(52) U.S. Cl.
CPC ...... *A61F 13/0236* (2013.01); *A61F 2013/00604* (2013.01); *A61F 2013/00859* (2013.01); *A61F 2013/00863* (2013.01)

(58) Field of Classification Search
CPC ........ A61F 13/0236; A61F 2013/00604; A61F 2013/00859; A61F 2013/000863; A61F 13/0246; A61F 13/0253; A61F 13/0263; A61F 13/0266
See application file for complete search history.

(56) References Cited

U.S. PATENT DOCUMENTS

| | | | | |
|---|---|---|---|---|
| 4,281,650 A | * | 8/1981 | Spiegelberg | A61F 15/001 206/440 |
| 4,561,435 A | * | 12/1985 | McKnight | A61F 13/0203 602/42 |
| 4,808,172 A | * | 2/1989 | Murata | A61F 13/0203 D24/189 |
| 4,972,829 A | * | 11/1990 | Knerr | A61F 13/0246 602/58 |
| 5,056,510 A | | 10/1991 | Gilman | |
| 5,062,418 A | * | 11/1991 | Dyer | A61F 13/00008 604/383 |
| 5,086,763 A | * | 2/1992 | Hathman | A61F 13/0246 602/42 |
| 5,090,406 A | | 2/1992 | Gilman | |
| 5,556,375 A | * | 9/1996 | Ewall | A61F 13/0203 602/54 |
| 5,662,598 A | | 9/1997 | Tobin | |

(Continued)

*Primary Examiner* — Camtu T Nguyen

(57) ABSTRACT

A breathable medical gauze patch includes at least one bandage body coupled with at least one ply of gauze or similar to, which not only helps wounds heal fast, but also prevent infections and potential complications. The at least one bandage body includes an adhesive on the underside that permits mounting about the wound site of a user/recipient. The at least one ply is disposed about a bandage aperture of the at least one bandage body. The at least one ply permits aeration therethrough to the wound site and facilitates absorption of any seepage of the wound while protecting the wound from the exterior environment. Further, the at least one ply may include multiple layers of sterilized medical grade gauze, a gel and an adhesive that allow the present invention to be efficiently and effectively applied to various deep or shallow wounds for facilitating speedy healing of the wounds.

5 Claims, 5 Drawing Sheets

(56) References Cited

U.S. PATENT DOCUMENTS

| | | | | |
|---|---|---|---|---|
| 6,174,544 B1* | 1/2001 | Jensen | ............... | A61L 15/28 |
| | | | | 424/443 |
| 8,314,283 B2 | 11/2012 | Kingsford et al. | | |
| 9,375,353 B2 | 6/2016 | Vitaris et al. | | |
| 9,517,164 B2* | 12/2016 | Vitaris | ............ | A61F 13/0203 |
| 2014/0200535 A1* | 7/2014 | Locke | ............ | A61M 1/782 |
| | | | | 604/321 |

* cited by examiner

BREATHABLE MEDICAL GAUZE PATCH

The current application claims a priority to the U.S. Provisional Patent application Ser. No. 62/850,857 filed on May 21, 2019.

FIELD OF THE INVENTION

The present invention relates generally to a medical device. More specifically, the present invention relates particularly to a wound dressing bandage with a center aerated aperture and at least one ply.

BACKGROUND OF THE INVENTION

Presently, the application of gauze patch to wounds is primarily accomplished through application of an arbitrary roll of gauze patch being applied to the wound site of an extraneous user with tape administered thereafter. While this particular manner of wound dressing is effective for niche medical applications, the conventional application is poorly served to address wounds requiring aeration such as burns, diabetic nerve damages, surgeries, scar tissues, abrasions, and any other wounds that are emotionally draining. For such applications, an application of plaster may additionally be necessitated to adequately dress the wound site which can be both tedious and resource draining when multiple wound dressings are required for prolonged treatment.

It is therefore the objective of the present invention to introduce a breathable medical gauze patch that provides an efficient and effective solution to addressing for small cuts, wounds, ulcers, diabetic wounds, cysts, post-surgery wounds, etc. The present invention serves as a convenient First-Aid kit at home, offices, gymnastics, restaurants, kitchens, and so on.

SUMMARY OF THE INVENTION

The present invention introduces a breathable medical gauze patch that includes at least one bandage body coupled with at least one ply of gauze patch or similar. The breathable medical gauze patch of the present invention not only helps any wounds heal fast, but also keeps wounds stay clean and thus prevents infections and potential complications. The at least one bandage body comprises an adhesive on the underside thereof that permits mounting about the wound site of the extraneous user/recipient. The at least one bandage body incorporates an adhesive border that is breathable, thus helps the present invention stay firmly in place, absorb leakages, protect the wound site, and does not cause skin irritations for sensitive skins or unpleasant stretching injuries when peeled off.

The at least one ply is disposed about a bandage aperture of the at least one bandage body through thereof. The at least one ply, made of high-quality, sterilized medical grade gauze patch, permits aeration therethrough to the wound site and comprises a plurality of perforations that enhances aeration to the wound site. Additionally, the at least one ply facilitates absorption of any seepage of the wound and offers protection from the exterior environment. Further, the at least one ply may include multiple layers of sterilized medical grade gauze patch, a gel and an adhesive that help addressing the wound, thus allowing the present invention to be effectively used for a variety of severities of wound.

The present invention facilitates stacking the at least one bandage body with a second bandage body to vary the thickness of the at least one ply in a stacked plurality thereof. Thus, the present invention permits the user to aerate a wound site through an adhesive dressing with a bandage aperture at the center thereof alongside a plurality of perforations disposed across the at least one ply. Further, the present invention may permit stacking through the underside adhesive disposed on the second surface that may be applied to the first surface of a preceding bandage body.

DETAIL DESCRIPTIONS OF THE INVENTION

Figure 1:
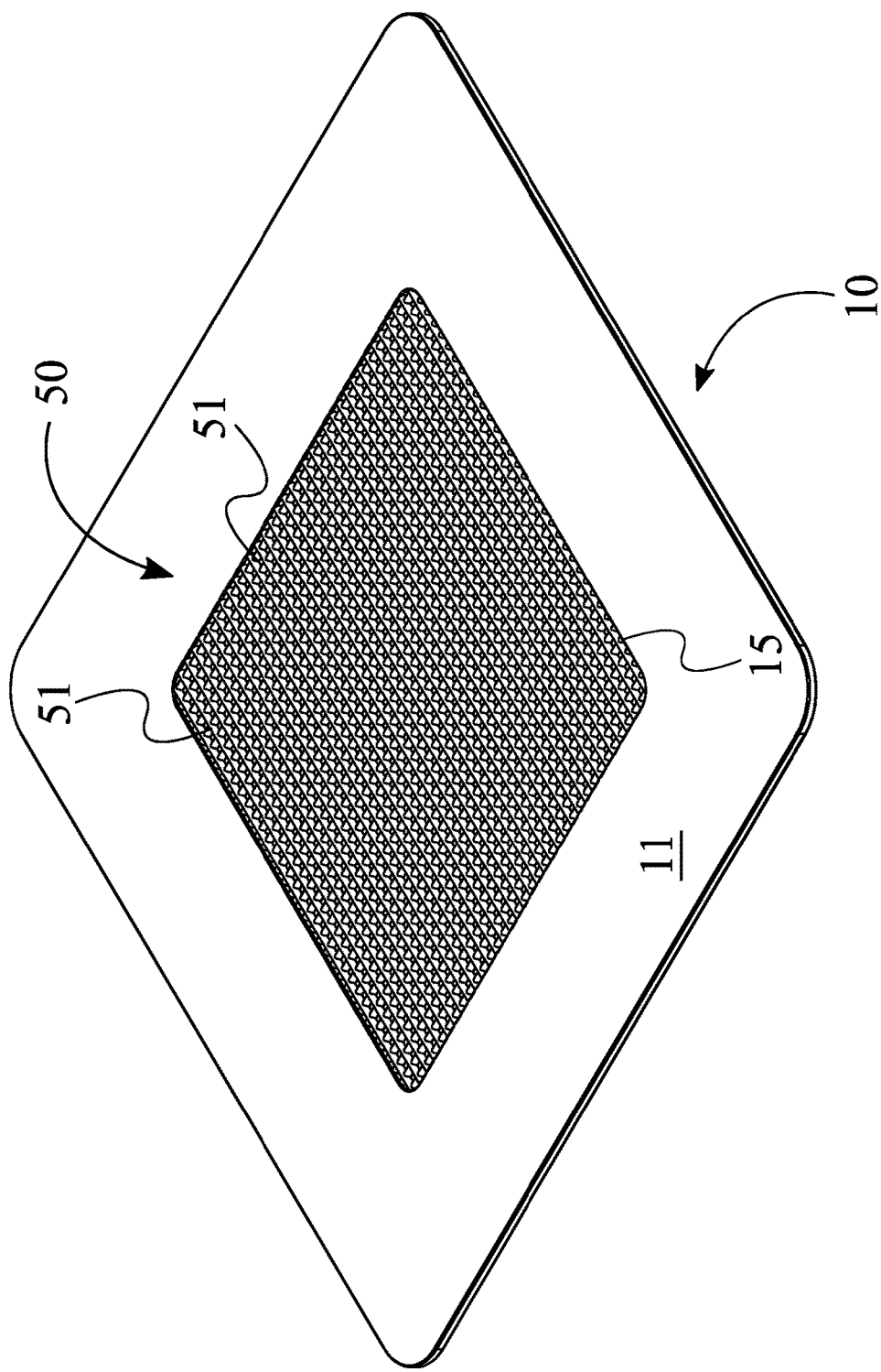
FIG. 1 is a top perspective view of the present invention, wherein a first surface is observed on the top of at least one bandage body with at least one ply within the bandage aperture at the center of the at least one bandage body.

All illustrations of the drawings are for the purpose of describing selected versions of the present invention and are not intended to limit the scope of the present invention.

The present invention comprises a breathable medical gauze patch that facilitates aeration to and absorption of seepage of a site of wound. The breathable medical gauze patch of the present invention utilizes high-quality, sterilized, medical grade gauze patch that keeps the wound clean and helps prevent infections or other complications including, but not limited to, sticking, infections, delays in your recovery, rashes, itchiness, and so on. Additionally, the breathable gauze patch offers maximum absorbency and superior aeration to adapt to any injury or open skin, whether it is a burn, bed sores/bed ulcers, burns cut, or graze, and absorbs blood. Further, the breathable medical gauze patch can be efficiently and effectively applied to various deep or shallow wounds through stacking multiple layers of the present invention and facilitate speedy healing of the wounds.

As can be seen in FIG. 1 to FIG. 5, the breathable medical gauze patch of the present invention comprises at least one bandage body 10 and at least one ply 50. The at least one bandage body 10 further comprises a first surface 11, a second surface 12, and a bandage aperture 15. The second surface 12 further comprises an adhesive 13 and a gel 14. The first surface 11 is terminally and longitudinally positioned on the at least one bandage body 10. The second surface 12 is positioned on the at least one bandage body 10 opposite and parallel with the first surface 11. The at least one ply 50 comprises a plurality of perforations 51. The at least one ply 50 is concentrically positioned on the at least one bandage body 50, and perimetrically attached to the at least one bandage body 10.

As can be seen in FIG. 1 to FIG. 5, the at least one bandage body 10 is disposed planarly coincident with the at least one ply 50 and connected therewith. The at least one bandage body 10 can be utilized to efficiently and effectively cling and conforms to various body contours for deep or shallow wounds. The at least one bandage body 10 preferably comprises a breathable material including, but not limited to, cloth, porous plastic, rubber, composites and so on. Additionally, the at least one bandage body 10 comprises a preferably rectilinear profile with an offset bandage aperture 15 thereof. The at least one bandage body 10 may comprise alternate planar geometries including, but not limited to, curvilinear, trilinear, polygonal, organic, and so on. Further, the at least one bandage body 10 may be stacked to accommodate additional plies to address a wound of varying severity. In the preferred embodiment of the present invention, the bandage aperture 15 traverses the center of the at least one bandage body 10. Thus, the bandage aperture 15 is located at the center of the at least one bandage body 10 and traversing normal therethrough. In other embodiments of the present invention, the bandage aperture 15 may be offset from the outer edges thereof and accommodate the at least one ply 50 therein or thereunder. Additionally, the bandage aperture 15 preferably comprises a rectilinear cross section but may alternately comprise geometry offset and lesser than the outer perimeter of the at least one bandage body 10. Further, the bandage aperture 15 may optionally comprise geometry disparate of the outer perimeter of the at least one bandage body 10 including, but not limited to, curvilinear, trilinear, polygonal, organic, and so on.

Figure 2:
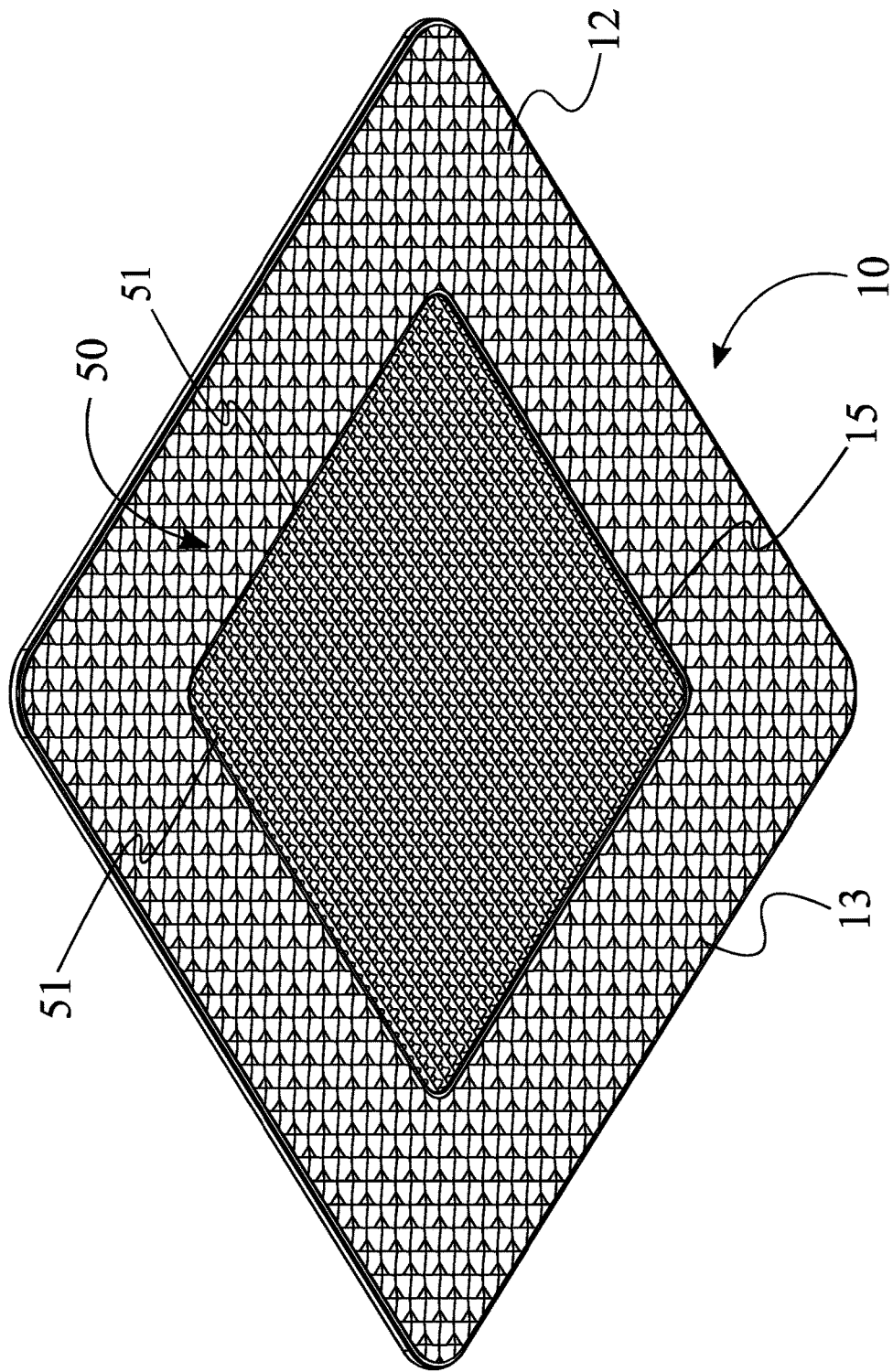
FIG. 2 is a bottom perspective view of the present invention, wherein an adhesive is observed beneath on a second surface of the at least one bandage body.
Figure 3:
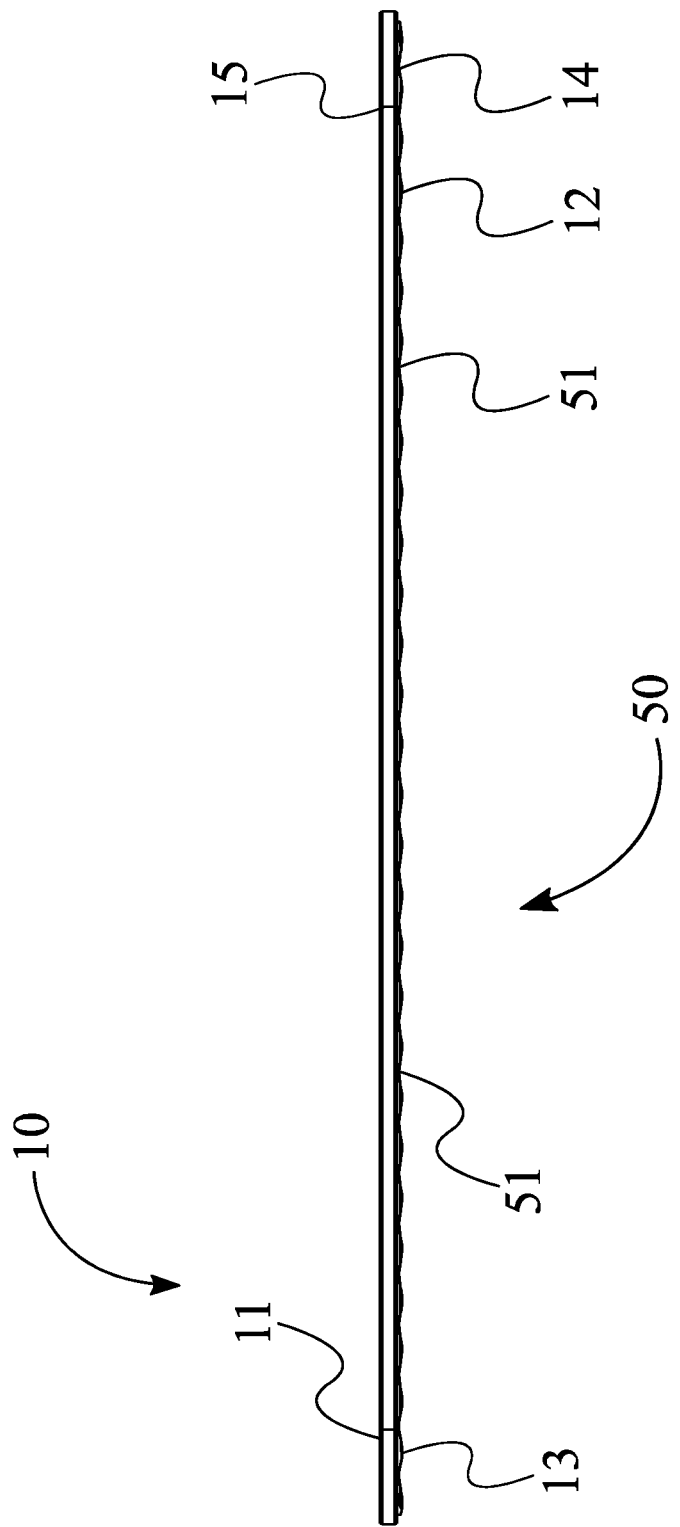
FIG. 3 is a front side view of the present invention, wherein the first surface is observed parallel with the second surface of the at least one bandage body.
Figure 4:
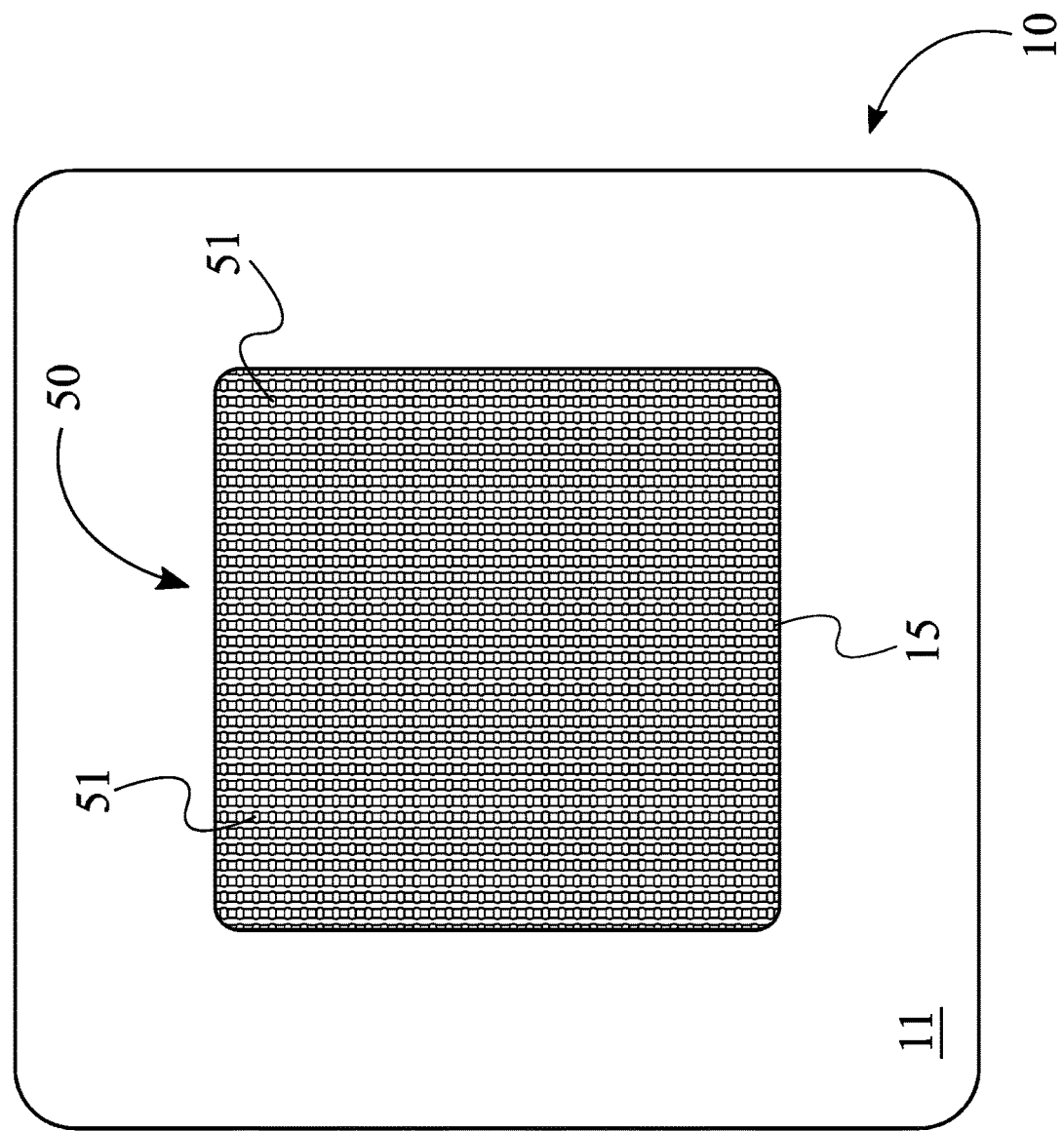
FIG. 4 is a top view of the present invention, wherein the first surface is observed congruent and overlying the second surface.

As can be seen in FIG. 1 to FIG. 5, the at least one ply 50 is positioned within the bandage aperture 15 of the at least one bandage body 10. Additionally, the at least one ply 50 is perimetrically attached to the bandage aperture 15 of the bandage body 10. In an alternative embodiment of the present invention, the at least one ply 50 is perimetrically attached to within the at least one bandage body 10 and between the first surface 11 and second surface 12 thereof, wherein edges of the at least one ply 50 are sandwiched between the first surface 11 and the second surface 12 of the bandage body 10, as can be seen in FIG. 3. The attachment of the at least one ply 50 to the bandage aperture 15 of the at least one bandage body 10, or directly to the bandage body 10 between the first surface 11 and the second surface 12, may be achieved through mounting mechanism including, but not limited to, gluing, sewing, fastening using common fasteners, etc. The at least one play 50 is preferably a gauze patch with a plurality of perforations 51 thereon. The at least one ply 50 preferably comprises a count of six to form six layers of gauze patch material, which may be stacked atop one another to bolster the absorbency of the at least one ply 50 or plurality thereof.

Additionally, the at least one ply 50 preferably comprises a geometry offset and greater than the bandage aperture 15, but lesser than the at least one bandage body 10 and is disposed adjacent with the adhesive 13. The at least one ply 50 preferably comprises a material including, but not limited to, gauze patch, bandage, high-quality cotton, open-weave cotton, medical grade gauze patch, medical grade bandage, sterilized gauze patch, sterilized bandage, crimped cushion, micro-fiber, any combinations thereof, and any other suitable material.

Further, alternate geometries may be employed including, but not limited to, rectilinear, curvilinear, trilinear, polygonal, organic, and so on. The at least one ply 50 is disposed centered and coincident or overlapping the bandage aperture 15, permitting the breathable medical gauze patch of the present invention to aerate beneath the at least one ply 50 or the plurality thereof. The plurality of perforations 51 is distributed across the at least one ply 40 and forms the matrix of a ply of gauze patch including, but not limited to, those used medically. Additionally, the plurality of perforations 51 traverses the at least one ply 50 and is distributed across the at least one ply 50. Further, the plurality of perforations 51 may be accomplished through a web or weaving of threads in a perpendicular matrix across or in substitution of the at least one ply 50. The plurality of perforations 51 may be coincident between adjacent individual plies of the at least one ply 50. Although the plurality of perforations 51 preferably overlaps indiscriminately therebetween adjacent plies to prevent seepage of the wound through the at least one ply 50 or the plurality thereof and the bandage aperture 15, while accommodating aeration therethrough to the wound site.

As can be seen in FIG. 1 to FIG. 5, the first surface 11 is disposed preferably on the top surface of the at least one bandage body 10, where the first surface 11 is opposite and parallel with the second surface 12. The first surface 11 preferably comprises a nonporous membrane or property thereat and providing a surface for the adhesive 13 of adjacent individual bandage bodies to adhere to. The first surface 11 further preferably possesses a surface congruent with the second surface 12. The second surface 12 is located preferably on the bottom surface of the at least one bandage body 10, where the second surface 12 is opposite and parallel with the first surface 11. The second surface 12 may optionally be coincident or adjacent and flush with the at least one ply 50, wherein the second surface 12 is adjacent and accommodates the adhesive 13 thereunder.

Figure 5:
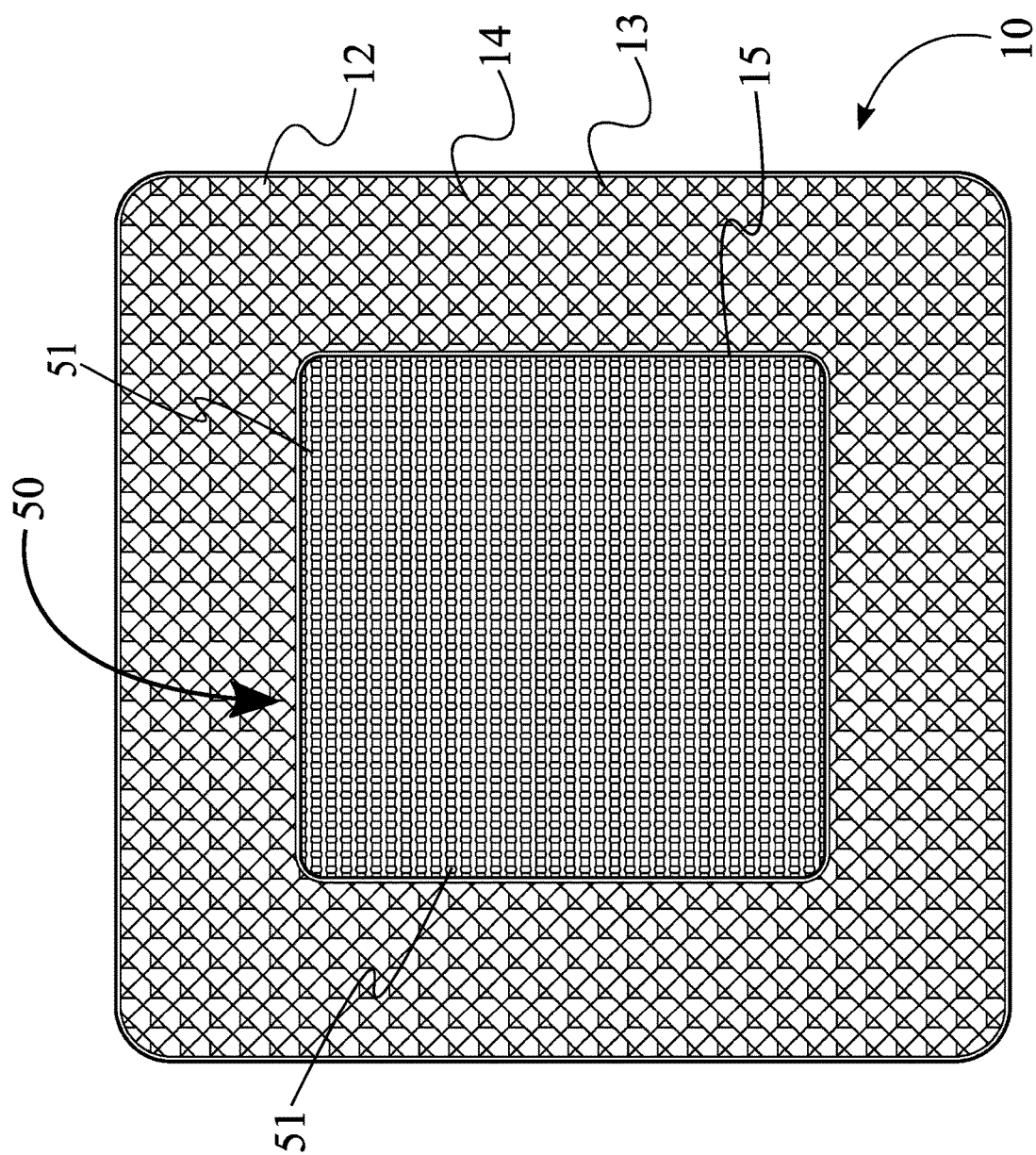
FIG. 5 is a bottom view of the present invention, wherein the second surface is observed congruent and underlying the first surface. Further observed is the adhesive located upon the second surface, offset and lesser than the outer perimeter of the at least one bandage body.

As can be seen in FIG. 2 to FIG. 3, and FIG. 5, the second surface 12 of the at least one bandage body 10 comprises the adhesive 13, which is terminally positioned on the second surface 12 opposite the first surface 11 and distributed across the second surface 13. More specifically, the adhesive 13 is adjacently located and parallel with the second surface 12 and may further be adjacently engaged with the at least one ply 50. Additionally, the adhesive 13 is preferably covered by an extraneous removable cover or packaging thereof. The adhesive 13 may further be intermixed with the optional gel 14 or adjacent thereto to mitigate seepage of the wound.

As can be seen in FIG. 3 and FIG. 5, the second surface 12 of the at least one bandage body 10 comprises the gel 14, which is terminally positioned on the second surface 12 opposite the first surface 11 and distributed across the second surface 12. More specifically, the gel 14 is disposed adjacently or intermixed with the adhesive 13 and may be located adjacent with the second surface 12. In an alternative embodiment of the present invention, the gel 14 may be concentrically arranged with the adhesive 13. Additionally, the gel 14 may comprise a sterilizing gel that exhibits sterilizing properties optionally to further assist in addressing a wound. Further, in alternative embodiment of the present invention, the gel 14 may comprise an adhesive.

Although the invention has been explained in relation to its preferred embodiment, it is to be understood that many other possible modifications and variations can be made without departing from the spirit and scope of the invention as hereinafter claimed.

What is claimed is:

1. A breathable medical gauze patch for facilitating aeriation to and absorption of seepage of a site of wound comprising:
    at least one bandage body;
    at least one ply;
    the at least one bandage body comprising a first surface, a second surface;

the first surface being terminally and longitudinally positioned on the at least one bandage body;
the second surface being positioned on the at least one bandage body opposite the first surface;
the at least one ply being concentrically positioned on the at least one bandage body;
the at least one ply being perimetrically attached to the at least one bandage body;
the at least one bandage body comprising a bandage aperture;
the bandage aperture traversing the center of the at least one bandage body;
the at least one ply being positioned within the bandage aperture of the at least one bandage body;
the at least one ply being perimetrically attached to the bandage aperture;
the at least one ply being perimetrically attached to within the at least one bandage body and between the first surface and second surface thereof;
the at least one ply comprising a plurality of perforations;
the plurality of perforations traversing the at least one ply;
the plurality of perforations being distributed across the at least one ply;
the second surface comprising an adhesive;
the adhesive being terminally positioned on the second surface opposite the first surface; and
the adhesive being distributed across the second surface.

2. The breathable medical gauze patch for facilitating aeriation to and absorption of seepage of a site of wound as claimed in claim 1, wherein the at least one ply comprises six layers.

3. The breathable medical gauze patch for facilitating aeriation to and absorption of seepage of a site of wound as claimed in claim 1 comprising:
the second surface comprising a gel;
the gel be terminally positioned on the second surface opposite the first surface; and
the gel being distributed across the second surface.

4. The breathable medical gauze patch for facilitating aeriation to and absorption of seepage of a site of wound as claimed in claim 3, wherein the gel comprises a sterilizing gel.

5. The breathable medical gauze patch for facilitating aeriation to and absorption of seepage of a site of wound as claimed in claim 3, wherein the gel comprises an adhesive.

\* \* \* \* \*